(12) United States Patent
Jeon

(10) Patent No.: US 11,890,247 B2
(45) Date of Patent: Feb. 6, 2024

(54) METHOD AND APPARATUS FOR PROVIDING BLOOD PRESSURE CONTROL MASSAGE

(71) Applicant: BODYFRIEND CO., LTD., Seoul (KR)

(72) Inventor: Chul Jin Jeon, Seoul (KR)

(73) Assignee: BODYFRIEND CO., LTD., Seoul (KR)

(*) Notice: Subject to any disclaimer, the term of this patent is extended or adjusted under 35 U.S.C. 154(b) by 533 days.

(21) Appl. No.: 17/251,613

(22) PCT Filed: Jun. 11, 2019

(86) PCT No.: PCT/KR2019/006985
§ 371 (c)(1),
(2) Date: Dec. 11, 2020

(87) PCT Pub. No.: WO2019/240457
PCT Pub. Date: Dec. 19, 2019

(65) Prior Publication Data
US 2021/0244605 A1    Aug. 12, 2021

(30) Foreign Application Priority Data
Jun. 14, 2018  (KR) .................. 10-2018-0067937

(51) Int. Cl.
*A61H 15/00*    (2006.01)

(52) U.S. Cl.
CPC .  *A61H 15/0078* (2013.01); *A61H 2015/0007* (2013.01); *A61H 2201/0149* (2013.01);
(Continued)

(58) Field of Classification Search
CPC ........ A61H 15/0078; A61H 2015/0007; A61H 2201/0149; A61H 2201/5048;
(Continued)

(56) References Cited

U.S. PATENT DOCUMENTS

| 6,106,576 A * | 8/2000 | Fromson ................. A61H 1/00 |
| | | 318/16 |
| 2006/0217641 A1* | 9/2006 | Tanizawa ............... A61H 23/02 |
| | | 601/100 |

(Continued)

FOREIGN PATENT DOCUMENTS

| CN | 102772292 A | 11/2012 |
| CN | 104799837 A | 7/2015 |

(Continued)

*Primary Examiner* — Justine R Yu
*Assistant Examiner* — Matthew R Moon
(74) *Attorney, Agent, or Firm* — Bridgeway IP Law Group, PLLC; Sang Ho Lee; Hyun Woo Shin

(57) ABSTRACT

Disclosed herein are a method and apparatus for providing a blood pressure control massage. According to an embodiment of the present disclosure, there is disclosed a method for providing blood pressure control massage, the method including acquiring blood pressure information of a user, determining a blood pressure control massage pattern on the basis of the blood pressure information, and providing a massage on the basis of the determined massage pattern.

20 Claims, 5 Drawing Sheets

(52) U.S. Cl.
CPC ............... *A61H 2201/5048* (2013.01); *A61H 2230/305* (2013.01); *A61H 2230/405* (2013.01); *A61H 2230/705* (2013.01)

(58) Field of Classification Search
CPC ........ A61H 2230/305; A61H 2230/405; A61H 2230/705; A61H 2201/5007; A61H 2201/5058; A61H 2203/0431; A61H 9/0078; A61H 2205/062; A61H 2205/081; A61H 2205/10; A61H 2205/12; A61H 7/004; A61H 7/007; A61H 2201/5023; A61B 5/00; A61B 5/021; A61B 5/4869
See application file for complete search history.

(56) References Cited

U.S. PATENT DOCUMENTS

2008/0269629 A1* 10/2008 Reiner ................. A61B 5/6831
600/544
2015/0366746 A1* 12/2015 Ashby .................... G16H 40/63
601/49
2017/0348177 A1* 12/2017 Inada ..................... G08B 21/18
2017/0348188 A1* 12/2017 Inada ..................... G01G 19/52
2020/0170882 A1* 6/2020 Park ..................... A61H 9/0078

FOREIGN PATENT DOCUMENTS

| | | |
|---|---|---|
| CN | 204542099 U | 8/2015 |
| CN | 106725539 A | 5/2017 |
| JP | 2010-213773 A | 9/2010 |
| KR | 10-2008-0032888 A | 4/2008 |
| KR | 10-2008-0088754 A | 10/2008 |
| KR | 10-2017-0137628 A | 12/2017 |
| KR | 10-1833317 B1 | 2/2018 |
| KR | 10-1858927 B1 | 5/2018 |
| WO | WO-9723254 A1 * | 7/1997 ............ A61M 21/00 |
| WO | 2018/066678 A1 | 4/2018 |

\* cited by examiner

METHOD AND APPARATUS FOR PROVIDING BLOOD PRESSURE CONTROL MASSAGE

TECHNICAL FIELD

The present disclosure relates to a blood pressure control massage, and more particularly, to a method and apparatus for providing a blood pressure control massage.

BACKGROUND ART

A massage is an adjuvant therapy in which mechanical stimuli in various forms are applied to a part of a subject's body by rubbing, pressing, pulling, tapping, or moving the part of the body to adjust modulation of the subject's body, aid circulation, and relieve the subject's fatigue.

For economic and time reasons, an increase in demand for massages has caused an increase in demand for massage apparatuses or massage devices that provide artificial massage functions. That is, with an increase in demand to relieve fatigue or stress by relaxing tight muscles through massage, various massage apparatuses which are efficient in terms of time and cost have been launched.

In recent years, beyond simply providing a massage function, massage apparatuses have been transformed into electronic devices that provide various additional functions and/or medical functions. Accordingly, research on a method of efficiently controlling a massage apparatus has been continuously carried out.

DISCLOSURE

Technical Problem

One objective of the present disclosure is to provide a blood pressure control massage.

Technical Solution

According to an embodiment of the present disclosure, there is disclosed a method for providing a blood pressure control massage, the method including acquiring blood pressure information of a user, determining a blood pressure control massage pattern on the basis of the blood pressure information, and providing a massage on the basis of the determined massage pattern.

According to another embodiment of the present disclosure, there is disclosed a massage apparatus including: a controller configured to acquire blood pressure information of a user, determine a blood pressure control massage pattern on the basis of the blood pressure information, and provide a massage on the basis of the determined massage pattern; and a massage module configured to provide a mechanical stimulus to at least a part of the user's body according to control of the controller.

DESCRIPTION OF DRAWINGS

Various aspects will be described below with reference to the drawings. Here, similar reference numerals will be used to refer to substantially similar elements. In the following embodiments, for the sake of description, a plurality of specific details will be proposed to provide overall understanding of one or more aspects. However, it is apparent that the aspect(s) may be embodied without the specific details.

In other examples, known structures and apparatuses are illustrated as block diagrams to facilitate description of one or more aspects.

BEST MODE OF THE INVENTION

Figure 1:
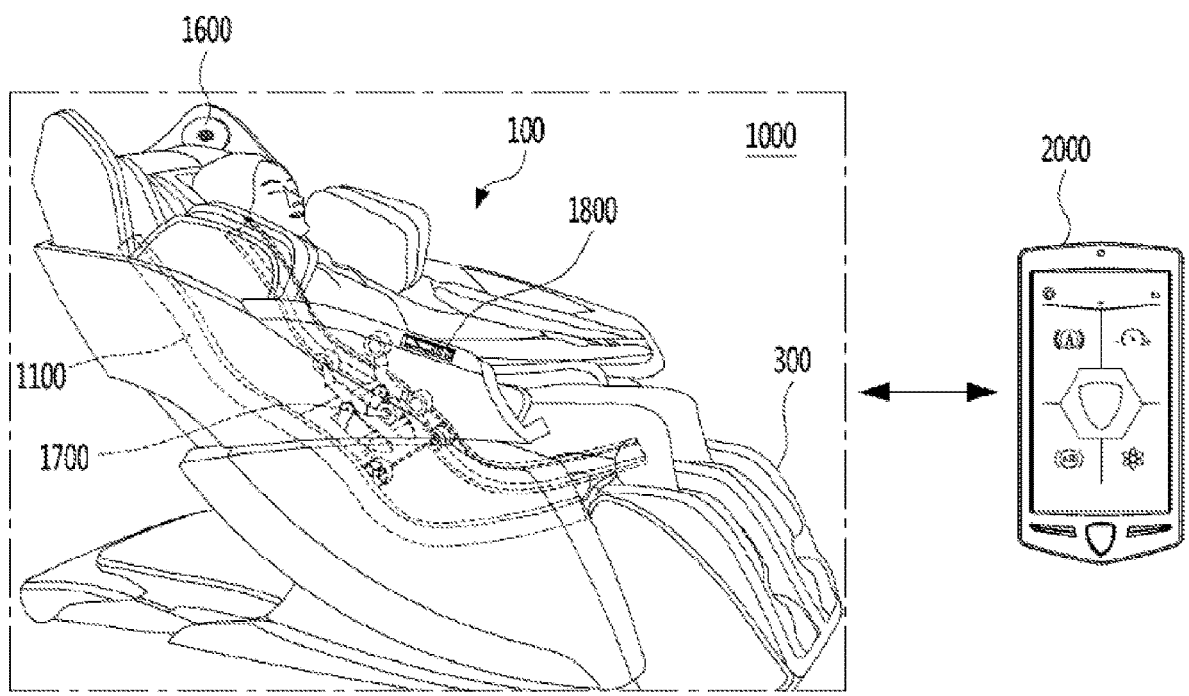
FIG. 1 is a view for describing a massage apparatus (1000) according to an embodiment of the present disclosure.

A method for providing a blood pressure control massage, the method including acquiring blood pressure information of a user, determining a blood pressure control massage pattern on the basis of the blood pressure information, and providing a massage on the basis of the determined massage pattern.

[Modes of the Invention]

The objects, features, and advantages of the present disclosure described above will become more apparent through the following embodiments relating to the accompanying drawings. The following descriptions of specific structures or functions are only given to describe embodiments according to the concept of the present disclosure. The embodiments according to the concept of the present disclosure may be embodied in various forms, and the present disclosure should not be interpreted as being limited by the embodiments described in the present specification or application.

Since the embodiments according to the concept of the present disclosure may be changed in various ways and have various forms, specific embodiments are illustrated in the drawings and will be described in detail in the present specification or application. However, this does not limit the embodiments according to the concept of the present disclosure to specific disclosed forms, and all changes, equivalents, and substitutes included in the idea and technical scope of the present disclosure should be construed as belonging to the embodiments according to the concept of the present disclosure.

Terms such as first and/or second may be used to describe various elements, but the elements are not limited by the terms. The terms are only used for the purpose of distinguishing one element from another element. For example, without departing from the scope according to the concept of the present disclosure, a first element may be referred to as a second element and, likewise, a second element may also be referred to as a first element.

When it is mentioned that a certain element is "connected" or "linked" to another element, although the certain element may be directly connected or linked to the other element, it should be understood that another element may be present therebetween. On the other hand, when it is mentioned that a certain element is "directly connected" or "directly linked" to another element, it should be understood that another element is not present therebetween. Other expressions used to describe a relationship between elements, i.e., "between" and "directly between" or "adjacent" and "directly adjacent," should be interpreted likewise.

Terms used in the present specification are only used to describe specific embodiments and are not intended to limit the present disclosure. A singular expression includes a plural expression unless the context clearly indicates otherwise. In the specification, terms such as "include" or "have" should be understood as designating that features, number, steps, operations, elements, parts, or combinations thereof are present and not as precluding the presence of or the possibility of adding one or more other features, numbers, steps, operations, elements, parts, or combinations thereof in advance.

Unless otherwise defined, all terms including technical or scientific terms used herein have the same meaning as commonly understood by those of ordinary skill in the art to which the present disclosure pertains. Terms, such as those defined in commonly used dictionaries, should be construed as having a meaning that is consistent with their meaning in the context of the relevant art and are not to be construed in an idealized or overly formal sense unless expressly so defined herein.

In the present specification, an actuator refers to an element capable of providing a driving force. Examples of the actuator may include a motor, a linear motor, an electronic motor, a DC motor, an AC motor, a linear actuator, an electric actuator, and the like, but the present disclosure is not limited thereto.

In the present specification, a spiral rod refers to a linear member having a spiral groove and may be implemented with a metal material. Examples of the spiral rod may include a cylindrical bar having a spiral groove formed in a surface thereof. Examples of the spiral rod may also include a metal lead screw.

According to an embodiment of the present disclosure, a massage apparatus may refer to a massage apparatus including a body massage part and a leg massage part.

Also, according to another embodiment, a body massage part 100 and a leg massage part 300 may be present as separate devices (for example, a body massage device and a leg massage device), and a massage apparatus may refer to the body massage device or the leg massage device.

Hereinafter, embodiments of the present disclosure will be described in more detail with reference to the accompanying drawings.

FIG. 1 is a view for describing a massage apparatus 1000 according to an embodiment of the present disclosure.

The massage apparatus 1000 according to an embodiment of the present disclosure may include a body massage part 100 that has an area formed to accommodate at least a portion of a user's body and is configured to massage the user's torso and a leg massage part 300 configured to massage the user's legs.

The body massage part 100 may provide a massage to at least a portion of the user's body. The body massage part 100 may include a massage module 1700 configured to provide a massage function to at least a portion of the user's body, an audio output module 1600 configured to provide an audio output in an arbitrary form to the user, a main frame 1100 constituting a framework of the body massage part 100, and a user input part 1800 configured to receive an input in an arbitrary form from the user.

The above-described elements that the body massage part 100 includes are merely an exemplary embodiment, and the body massage part 100 may include various elements other than those described above.

Also, the shape and structure of the massage apparatus 1000 illustrated in FIG. 1 are merely illustrative, and a massage apparatus 1000 having various other forms may also fall within the scope of the present disclosure unless the form of the massage apparatus 1000 deviates from the scope defined by the claims of the present disclosure.

The body massage part 100 may have a space formed in an arbitrary shape to accommodate a user. The body massage part 100 may have a space formed in a shape that corresponds to a shape of the user's body. For example, as illustrated in FIG. 1, the body massage part 100 may be implemented in the shape of a chair that may accommodate the entire body of the user or a portion of the body.

A portion of the body massage part 100 that comes in contact with the ground may include an arbitrary material configured to increase a frictional force or an arbitrary member configured to increase a frictional force (e.g., a nonslip pad etc.) and may include a wheel configured to reinforce the mobility of the massage apparatus 1000.

At least a portion of the body massage part 100 may be able to slide. For example, in the case in which the body massage part 100 begins to perform a massage, at least a portion of the body massage part 100 may slide forward. Also, the body massage part 100 may be reclined. As a result, the body massage part 100 may provide a massage while being reclined.

According to an embodiment of the present disclosure, the massage apparatus 1000 may include at least one air cell (not illustrated). The air cell may be located at portions of the massage apparatus 1000 that correspond to the user's shoulders and pelvis, the arm massage parts, the leg massage part 300, and the like, but the present disclosure is not limited thereto, and the air cell may be disposed at various other portions of the massage apparatus 1000.

The massage apparatus 1000 may include an air supply part. The air supply part may supply air to the air cell to inflate the air cell. The air supply part may be located inside the body massage part 100 or located at the leg massage part 300. Also, the air supply part may be located outside the massage apparatus 1000.

The leg massage part 300 may provide a leg massage to the user. For example, the leg massage part 300 may include a calf massage part configured to massage a user's calf and/or a foot massage part configured to massage a user's foot.

A length of the leg massage part 300 may be adjustable according to characteristics of the user's body. For example, in a case in which a tall user uses the massage apparatus 1000, since the length of the user's calf is long, it is necessary to increase the length of the leg massage part 300. Also, in a case in which a short user uses the massage apparatus 1000, since the length of the user's calf is short, it is necessary to decrease the length of the leg massage part 300. Accordingly, the leg massage part 300 may provide a leg massage that is customized to a height of the user.

The massage module 1700 may be disposed inside the body massage part 100 so as to provide mechanical stimuli in arbitrary forms to a user accommodated in the body massage part 100. As illustrated in FIG. 1, the massage module 1700 may move along the main frame 1100 disposed inside the body massage part 100.

For example, a rack gear may be disposed at the main frame 1100 of the body massage part 100, and the massage module 1700 may, while moving along the rack gear, provide mechanical stimuli to various parts of the user's body. The massage module 1700 may include a ball massage unit or a roller massage unit, but the present disclosure is not limited thereto.

The main frame 1100 constitutes a framework of an internal configuration of the body massage part 100 and may be implemented with a metal material, a plastic material, or the like. For example, the main frame 1100 may be implemented with iron, alloys, steel, and the like, but the present disclosure is not limited thereto, and the main frame 1100 may also be implemented with various other rigid materials.

According to an embodiment of the present disclosure, the massage apparatus 1000 may include the audio output module 1600. The audio output module 1600 may be disposed at various locations. For example, the audio output module 1600 may include a plurality of output units such as an upper-end audio output unit disposed at an upper end of a seat part coming in contact with the user, a front audio output unit attached to front ends of the arm massage parts at the left and right sides of the seat part, and/or a rear audio output unit attached to rear ends of the arm massage parts, but the present disclosure is not limited thereto. In this case, the audio output module 1600 may provide stereophonic sound such as 5.1 surround sound, but the present disclosure is not limited thereto.

According to an embodiment of the present disclosure, the user may control the massage apparatus 1000 using a massage apparatus control device 2000. The massage apparatus control device 2000 may be connected to the massage apparatus 1000 through wired communication and/or wireless communication.

The massage apparatus control device 2000 may include a remote controller, a cellular phone, a personal digital assistant (PDA), and the like, but the present disclosure is not limited thereto, and the massage apparatus control device 2000 may include various other electronic devices that may be connected to the massage apparatus 1000 through wired or wireless communication.

Figure 2:
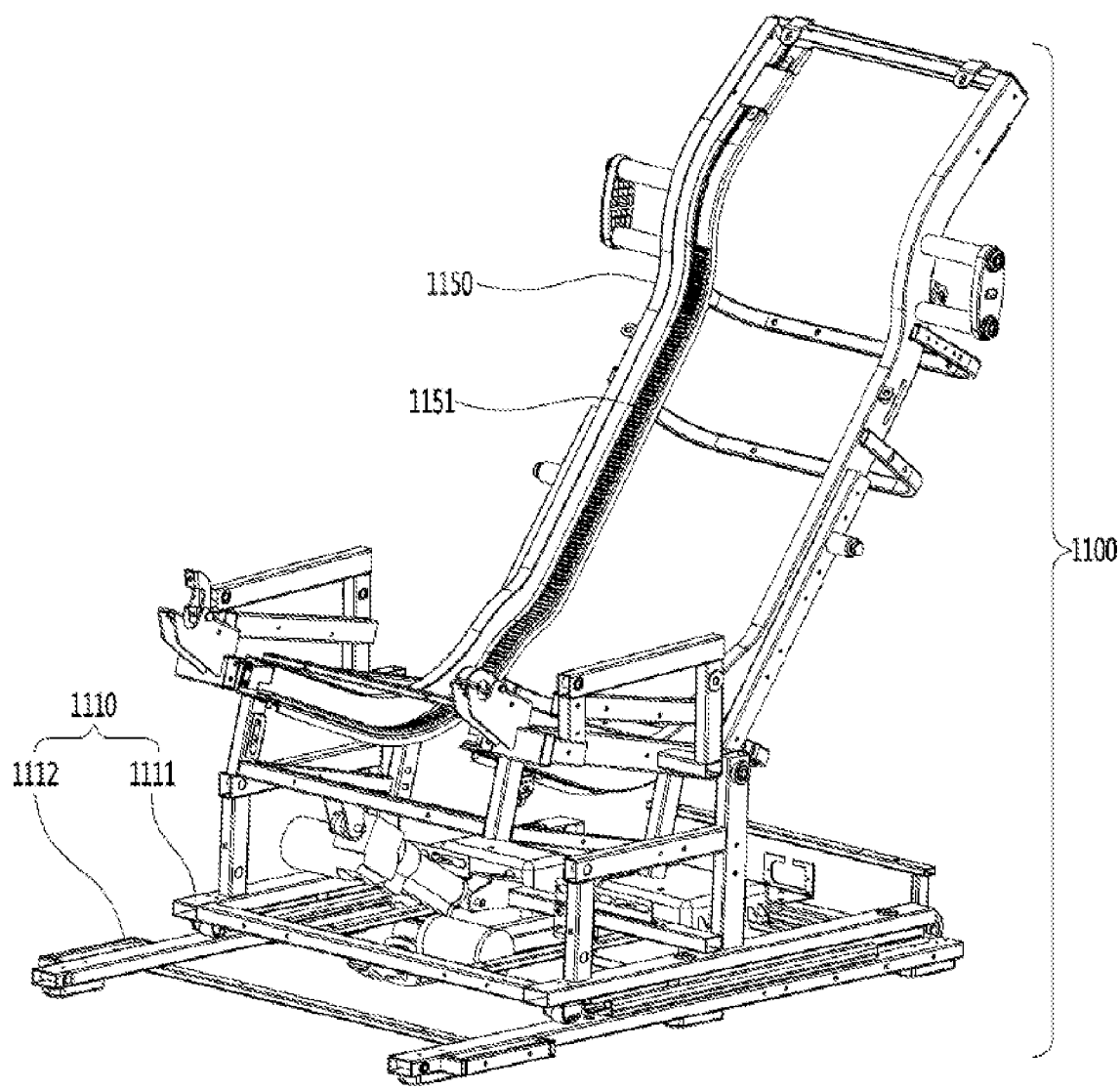
FIG. 2 is a view for describing a main frame according to an embodiment of the present disclosure.

FIG. 2 is a view for describing the main frame according to an embodiment of the present disclosure.

According to an embodiment of the present disclosure, the main frame 1000 may include an upper frame 1150 on which the massage module 1700 is provided and a base frame 1110 configured to support the upper frame 1150.

A rack gear 1151 may be disposed on at least a portion of the upper frame 1150. The rack gear 1151 is a member configured to guide the vertical movement of the massage module 1700 and may include a plurality of valley portions and a plurality of ridge portions.

According to an embodiment of the present disclosure, the rack gear 1151 may be disposed to face both side portions of the upper frame 1150, and the massage module 1700 may move along the rack gear 1151.

For example, the massage module 1700 may include a gear engaged with the rack gear 1151, and as the gear rotates due to an actuator disposed in the massage module 1700, the massage module 1700 may move upward or downward.

The rack gear 1151 may be implemented with a metal material or a plastic material. For example, the rack gear 1151 may be implemented with iron, steel, alloys, reinforced plastic, a melamine resin, a phenol resin, and the like, but the present disclosure is not limited thereto.

The upper frame 1150 may be implemented in various shapes. For example, the upper frame 1150 may be classified into an S-frame, an L-frame, an S&L frame, or a double S&L frame according to its shape, but the present disclosure is not limited thereto.

The S-frame refers to the upper frame 1150 in which at least a portion is curved in an S-like shape. The L-frame refers to the upper frame 1150 in which at least a portion is bent in an L-like shape, the S&L frame refers to a frame that includes both a portion curved in an S-like shape and a portion bent in an L-like shape, and the double S&L frame refers to a frame that includes a portion bent in an L-like shape and two portions curved in an S-like shape.

The base frame 1110 refers to a portion of the main frame 1100 that supports the upper frame 1150 and comes in contact with the ground. The base frame 1110 may include a base upper frame 1111 and a base lower frame 1112.

The base upper frame 1111 may support the upper frame 1150, and the base lower frame 1112 may come in contact with the ground. Also, the base upper frame 1111 may be located so as to come in contact with the base lower frame 1112.

According to an embodiment of the present disclosure, the base upper frame 1111 may move along the base lower frame 1112. For example, the base upper frame 1111 may slide forward or rearward along the base lower frame 1112. In this case, the upper frame 1150 may be connected to the base upper frame 1111 and move according to the movement of the base upper frame 1111.

For example, in the case in which the base upper frame 1111 moves forward, the upper frame 1150 may also move forward, and in the case in which the base upper frame 1111 moves rearward, the upper frame 1150 may also move rearward. Thus, sliding of the body massage part 100 may be allowed.

Specifically, in order to allow the movement of the base upper frame 1111, a moving wheel may be disposed at a lower portion of the base upper frame 1111. Also, a guide member configured to guide the moving wheel may be disposed at an upper portion of the base lower frame 1112. The moving wheel disposed at the base upper frame 1111 may move along the guide member disposed at the base lower frame 1112 so that forward movement or rearward movement of the base upper frame 1111 is allowed.

According to another embodiment of the present disclosure, the massage apparatus 1000 may not provide a sliding function and, in this case, the base frame 1110 may not be separated into upper and lower frames.

Figure 3:
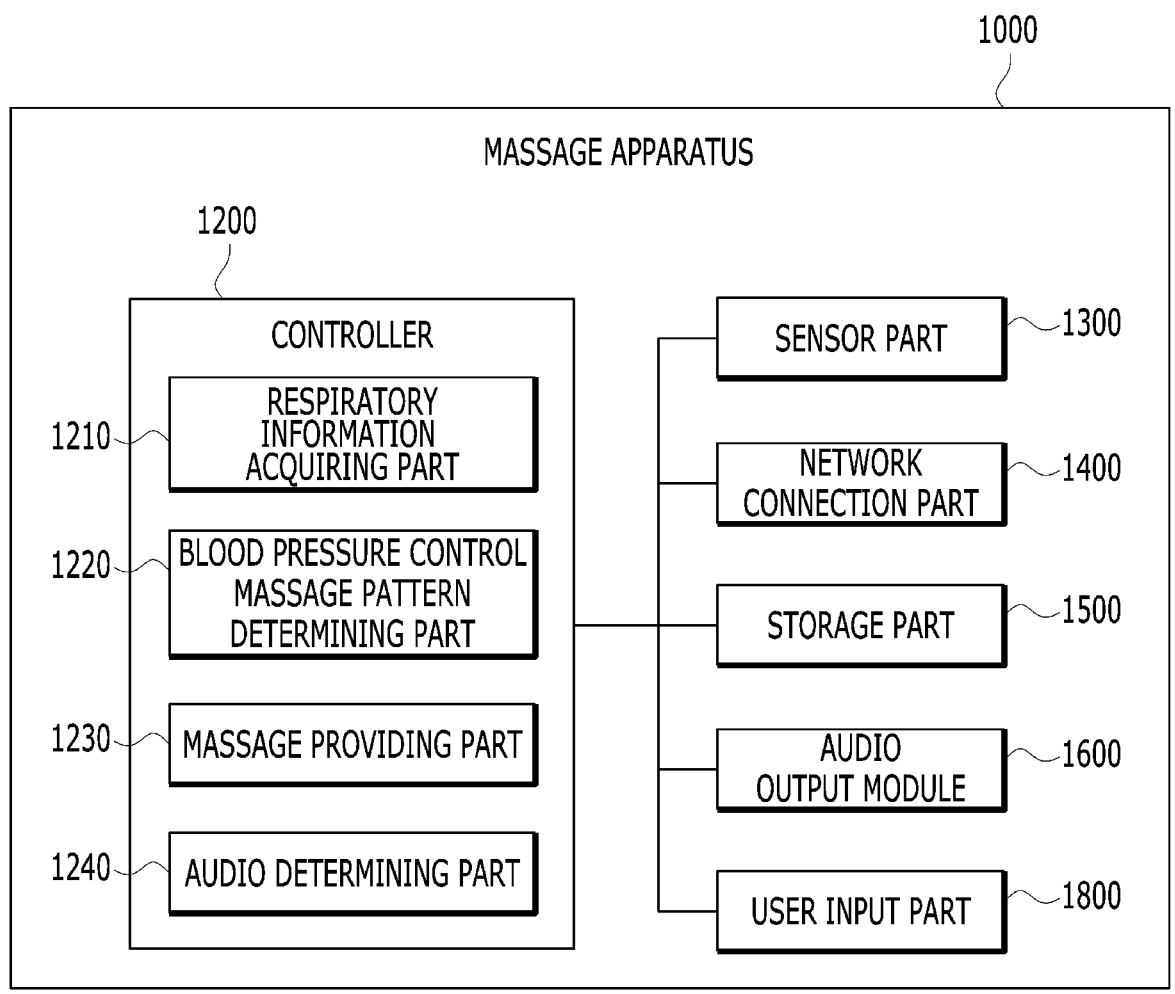
FIG. 3 is a view for describing elements of the massage apparatus (1000) according to an embodiment of the present disclosure.

FIG. 3 is a view for describing the elements of the massage apparatus 1000 according to an embodiment of the present disclosure.

According to an embodiment of the present disclosure, the massage apparatus 1000 may include at least one of a controller 1200, a sensor part 1300, the user input part 1800, the audio output module 1600, and a network connection part 1400.

The controller 1200 may control the operation of the massage apparatus 1000. The controller 1200 may be implemented with a single processor or implemented with a plurality of processors. In a case in which the controller 1200 is implemented with a plurality of processors, at least some of the plurality of processors may be located to be physically spaced apart at a certain distance. The controller 1200 is not limited thereto and may be implemented in various other ways.

According to an embodiment of the present disclosure, the controller 1200 may control the operation of the massage apparatus 1000. For example, the massage apparatus 1000 may include a plurality of actuators, and the controller 1200 may control the operation of the plurality of actuators to control the operation of the massage apparatus 1000. For example, the massage apparatus 1000 may include a massage module 1700 moving actuator, at least one actuator included in the massage module, and at least one of a back angle actuator, a leg angle actuator, a foot massage actuator, a leg length adjusting actuator, and a sliding actuator, and the controller 1200 may control the actuators to control the operation of the massage apparatus 1000.

The massage module moving actuator is an actuator that allows vertical movement of the massage module 1700, and the massage module 1700 may move along the rack gear due to the operation of the massage module 1700 moving actuator.

The back angle actuator is an actuator that adjusts an angle of a portion of the massage apparatus 1000 that comes in contact with the user's back, and the back angle of the massage apparatus 1000 may be adjusted due to the operation of the back angle actuator.

The leg angle actuator is an actuator that adjusts an angle of the leg massage part 300 of the massage apparatus 1000, and an angle between the leg massage part 300 and the body massage part 100 may be adjusted due to the operation of the leg angle actuator.

The foot massage actuator refers to an actuator that operates a foot massage module included in the leg massage part 300. The massage apparatus 1000 may utilize the foot massage actuator to provide a foot massage to the user.

At least one actuator may be included in the massage module 1700, and the controller 1200 may operate the at least one actuator to provide various massage operations. For example, the controller 1200 may operate at least one actuator included in the massage module 1700 to provide a tapping massage, a rubbing massage, and the like, but the present disclosure is not limited thereto, and the controller 1200 may provide various other massage operations.

The leg length adjusting actuator refers to an actuator that adjusts the length of the leg massage part 300. For example, the controller 1200 may utilize the leg length adjusting actuator to adjust the length of the leg massage part 300 to suit each user, and as a result, a user may receive a massage that is suitable for his or her body frame.

The sliding actuator allows sliding of the massage apparatus 1000. For example, a horizontal base upper frame 1114a may move forward or rearward due to the operation of the sliding actuator, and as a result, an upper frame connected to the horizontal base upper frame 1114a may move forward or rearward.

The sensor part 1300 may use at least one sensor to acquire various pieces of information. Examples of the sensor may include a pressure sensor, an infrared sensor, a light emitting diode (LED) sensor, and the like but are not limited thereto.

Also, the sensor part 1300 may include a biometric information acquisition sensor. The biometric information acquisition sensor may acquire fingerprint information, facial information, voice information, iris information, body weight information, electrocardiogram information, body composition information, and the like, but the present disclosure is not limited thereto, and the biometric information acquisition sensor may acquire various other pieces of biometric information.

According to another embodiment of the present disclosure, the massage apparatus 1000 may sense an area in contact with the user and/or a location of the area in contact with the user through sensors. Also, the massage apparatus 1000 may acquire shoulder position information of the user through the sensor part 1300. Also, the massage apparatus 1000 may provide a customized massage on the basis of the acquired information. For example, in the case in which the massage apparatus 1000 provides a shoulder massage, the massage apparatus 1000 may recognize the positions of the user's shoulders on the basis of information acquired through the sensor part 1300 and provide a shoulder massage to the user according to the result of recognition.

The user input part 1800 may receive a command related to operational control of the massage apparatus 1000 from the user, and the user input part 1800 may be implemented in various forms. For example, the user input part 1800 may be disposed in the body massage part 100 or disposed in the leg massage part 300, but the present disclosure is not limited thereto.

The massage apparatus 1000 may acquire various commands from the user through the user input part 1800. For example, the massage apparatus 1000 may receive an arbitrary command relating to selection of massage module, selection of massage type, selection of massage intensity, selection of massage time, selection of massage site, selection relating to location and operation of the body massage part 100, selection relating to on-off of power of the massage apparatus 1000, selection relating to whether to use warming function, selection relating to sound source playback, and the like, but the present disclosure is not limited thereto.

According to another embodiment of the present disclosure, the user input part 1800 may have, according to a function preset by the user, a function preset by itself, or the like, hot key buttons, and/or selection buttons for executing direction selection, cancellation, and input.

The user input part 1800 may be implemented with a key pad, a dome switch, a touch pad (static pressure/capacitive), a jog wheel, a jog switch, and the like, but the present disclosure is not limited thereto. Also, the user input part 1800 may acquire a command through the user's speech on the basis of a voice recognition technology.

According to an embodiment of the present disclosure, the user input part 1800 may include a display configured to display an operational status of the massage apparatus 1000, the current condition of the user, or the like. In this case, the display may be at least one of a liquid crystal display (LCD), a thin film transistor-liquid crystal display (TFT-LCD), an organic light-emitting diode (OLED) display, a flexible display, and a 3D display, but the present disclosure is not limited thereto.

The audio output module 1600 may provide an audio output in an arbitrary form to the user. For example, the audio output module 1600 may output a sound source and/or a binaural beat, which is optimized for a massage pattern provided from the massage apparatus 1000, to the user and provide brain stimulation to the user. The audio output module 1600 may output an acoustic signal which is received through a network (not illustrated) or stored in an internal/external storage medium (not illustrated). For example, through network connection (for example, Bluetooth connection etc.) with a user terminal 2000, the audio output module 1600 may output a sound source according to control of the user terminal 2000. Also, the audio output module 1600 may output an acoustic signal in an arbitrary form that is generated in relation to the operation of the massage apparatus 1000.

The massage apparatus 1000 according to an embodiment of the present disclosure may include the network connection part 1400. The network connection part 1400 may perform communication with a module inside the massage apparatus 1000, an external massage apparatus, and/or the user terminal 2000 through a network in an arbitrary form. The network connection part 1400 may include a wired/wireless connection module for network connection. For example, as a wireless connection technology, wireless LAN (WLAN) (Wi-Fi), wireless broadband (WiBro), World Interoperability for Microwave Access (WiMax), High Speed Downlink Packet Access (HSDPA), and the like may be used. For example, as a wired connection technology, x Digital Subscriber Line (xDSL), Fiber to the Home (FTTH), Power Line Communication (PLC), and the like may be used. Also, the network connection part may include a short-range communication module and transmit and receive data to and from an arbitrary apparatus/terminal located a short distance away. For example, as a short-range communication technology, Bluetooth, Radio Frequency Identification (RFID), Infrared Data Association (IrDA), Ultra Wideband (UWB), ZigBee, and the like may be used, but the present disclosure is not limited thereto.

A storage part 1500 may store various pieces of information relating to the massage apparatus 1000. For example, the storage part 1500 may include massage control information or include personal authentication information, but the present disclosure is not limited thereto.

The storage part 1500 may be implemented through a nonvolatile storage medium that may continuously store arbitrary data. For example, the storage part 1500 may include a disk, an optical disk, and a magneto-optical storage device and also include a flash memory and/or a storage device based on a battery-backup memory, but the present disclosure is not limited thereto.

Also, the storage part 1500 may include a memory. The memory may be a main storage device directly accessed by a processor and may refer to a volatile storage device in which stored information is erased instantaneously when the power is turned off, such as a random access memory (RAM) such as a dynamic random access memory (DRAM) and a static random access memory (SRAM), but the memory is not limited thereto. The memory may be operated by the controller 1200.

The controller 1200 may include at least one of a respiratory information acquiring part 1210, a blood pressure control massage pattern determining part 1220, a massage providing part 1230, and an audio determining part 1240.

According to an embodiment of the present disclosure, the controller 1200 may acquire blood pressure information of a user. For example, the controller 1200 may acquire blood pressure information of the user through the sensor part 1300, acquire blood pressure information of the user that is stored in the storage part 1500, or acquire blood pressure information from an external device, but the present disclosure is not limited thereto.

On the basis of the acquired blood pressure information, the controller 1200 may determine whether to provide a blood pressure control massage. For example, in a case in which a blood pressure is higher than a predetermined reference, the controller 1200 may determine to provide a blood pressure control massage. In this case, the predetermined reference may be determined by a pre-stored value. Also, the predetermined reference may be determined by blood pressure information acquired from users of the massage apparatus 1000. For example, the massage apparatus 1000 may apply a predetermined algorithm to the blood pressure information acquired from the users to analyze the blood pressure information and may determine the predetermined reference on the basis of the result of analysis.

According to an embodiment of the present disclosure, the blood pressure control massage pattern determining part 1220 may change a massage pattern selected by the user and determine the changed massage pattern as a blood pressure control massage pattern.

For example, the blood pressure control massage pattern determining part 1220 may determine a relatively slow massage pattern as a blood pressure control massage pattern. Specifically, even when a first user and a second user select the same massage pattern, in a case in which a blood pressure of the first user is higher than a blood pressure of the second user, the massage pattern selected by the first user may be modified to become relatively slower, and the modified massage pattern may be determined as a blood pressure control massage pattern for the first user.

Also, the blood pressure control massage pattern determining part 1200 may determine a relatively gentle massage pattern as a blood pressure control massage pattern. Specifically, even when a first user and a second user select the same massage pattern, in a case in which a blood pressure of the first user is higher than a blood pressure of the second user, the massage pattern selected by the first user may be modified to become relatively gentler, and the modified massage pattern may be determined as a blood pressure control massage pattern for the first user.

As another example, in a case in which a blood pressure of the first user is higher than or equal to (or exceeds) a predetermined threshold value, a massage pattern, of which a speed is slower by a predetermined value than a basic speed of the massage pattern selected by the user, may be determined as a blood pressure control massage pattern. In this case, blood pressures may be classified into a plurality of groups, and the blood pressure control massage pattern may be determined on the basis of a group to which a blood pressure of the user belongs. For example, blood pressures of users may be classified into three groups, and the slowest massage pattern may be provided to a user whose blood pressure belongs to the highest blood pressure group.

Also, in a case in which a blood pressure of the first user is higher than or equal to (or exceeds) a predetermined threshold value, a massage pattern, of which an intensity is lower by a predetermined value than a basic intensity of the massage pattern selected by the user, may be determined as a blood pressure control massage pattern. In this case, blood pressures may be classified into a plurality of groups, and the blood pressure control massage pattern may be determined on the basis of a group to which a blood pressure of the user belongs. For example, blood pressures of users may be classified into three groups, and the gentlest massage pattern may be provided to a user whose blood pressure belongs to the highest blood pressure group.

As another example, the blood pressure control massage pattern determining part 1220 may determine a massage pattern that has a gradually decreasing speed as a blood pressure control massage pattern. Specifically, in a case in which a blood pressure of the first user is high, at least a portion of the massage pattern selected by the first user may be modified to a massage pattern having a gradually decreasing speed, and the modified massage pattern may be determined as a blood pressure control massage pattern for the first user.

Also, the blood pressure control massage pattern determining part 1220 may determine a massage pattern that has a gradually decreasing intensity as a blood pressure control massage pattern. Specifically, in a case in which a blood pressure of the first user is high, at least a portion of the massage pattern selected by the first user may be modified to a massage pattern having a gradually decreasing intensity, and the modified massage pattern may be determined as a blood pressure control massage pattern for the first user.

In a case in which a high-intensity, high-speed massage is provided to a user with high blood pressure, sympathetic nerves may be activated and the user's blood pressure may become even higher. Therefore, according to an embodiment of the present disclosure, a gentle, low-speed massage is provided to a user with high blood pressure to activate parasympathetic nerves of the user and stabilize respiration so that the user's blood pressure is decreased.

According to another embodiment of the present disclosure, the blood pressure control massage pattern determining part 1220 may determine a respiratory guide pattern on the basis of a blood pressure, generate a massage pattern including the determined respiratory guide pattern, and determine the generated massage pattern as a blood pressure control massage pattern.

The respiratory guide pattern is a massage pattern for guiding the respiration of a user and may include a pattern in which the chest and/or back of the user is pushed. In this case, the massage module 1700 may not only move in a vertical direction but also move forward and/or rearward (for example, in a direction in which the user is located and a direction opposite thereto), and the respiratory guide pattern may cause the massage module 1700 to move forward (for example, in a direction in which the user is located) to push the user.

For example, in a case in which blood pressure information of the user indicates high blood pressure, the number of times the massage module 1700, which moves according to the respiratory guide pattern, pushes the chest and/or back of the user may start from a predetermined value and then gradually decrease over time. Specifically, the number of times the massage module 1700, which moves according to the respiratory guide pattern, pushes the chest and/or back of the user may start from 12 per unit time and then decrease to 10 over time.

Also, in a case in which blood pressure information of the user indicates high blood pressure, the number of times the massage module 1700, which moves according to the respiratory guide pattern, pushes the chest and/or back of the user may start from a number of times that corresponds to an acquired respiratory rate and then gradually decrease over time.

In this case, the number of times corresponding to the respiratory rate may be determined on the basis of respiratory rate information of the user that is acquired by the respiratory information acquiring part 1210. The respiratory rate information of the user may refer to information on the number of times the user breathes within a predetermined amount of time. For example, the sensor part 1300 may sense respiratory sounds of the user and measure the number of times the user breathes within a specific amount of time (for example, the number of times the user breathes per minute) on the basis of the sensed sounds, and the respiratory information acquiring part 1210 may acquire a measurement result.

Also, the sensor part 1300 may measure a respiratory rate through a pressure sensor, and the respiratory information acquiring part 1210 may acquire information on the measured respiratory rate.

Also, the sensor part 1300 may include a photoplethysmography (PPG) sensor and sense a respiratory rate through light.

According to an embodiment, the respiratory information acquiring part 1210 may acquire as many respiratory rates as a predetermined number of measurements and obtain an average value of the measured respiratory rates to acquire respiratory rate information. Also, the respiratory information acquiring part 1210 may acquire as many respiratory rates as a predetermined number of unit times and obtain an average value of the respiratory rates measured per unit time to acquire respiratory rate information.

Upon inhalation, the size of the chest cavity increases and the chest is expanded forward, and upon exhalation, the size of the chest cavity decreases and the chest is contracted rearward. Respiration of the user may be guided using a 3D massage module 1700 to change the respiration of the user. Also, by changing the respiration of the user, the user's blood pressure may be controlled.

According to another embodiment of the present disclosure, the blood pressure control massage pattern determining part 1220 may acquire preferred massage pattern information of the user and additionally utilize the acquired preferred massage pattern information to determine a blood pressure control massage pattern.

The blood pressure control massage pattern determining part 1220 may acquire preferred massage pattern information of the user.

For example, the blood pressure control massage pattern determining part 1220 may acquire preferred massage pattern information of the user that is stored in the storage part 1500. Also, the blood pressure control massage pattern determining part 1220 may acquire preferred massage pattern information of the user from an external device (for example, a remote controller, a user terminal, etc.) through the network connection part 1400.

Also, the blood pressure control massage pattern determining part 1220 may process the preferred massage pattern information of the user to determine a blood pressure control massage pattern.

For example, in a case in which blood pressure information of the user indicates a relatively high blood pressure, the blood pressure control massage pattern determining part 1220 may process a preferred massage pattern of the user to become slow (and/or become gradually slower) to determine a blood pressure control massage pattern. Also, the blood pressure control massage pattern determining part 1220 may add a predetermined massage pattern to the preferred massage pattern of the user (and/or replace the preferred massage pattern of the user with the predetermined massage pattern) on the basis of the blood pressure information to determine a blood pressure control massage pattern. Specifically, in a case in which blood pressure information of the user indicates a relatively higher blood pressure compared to another user, the blood pressure control massage pattern determining part 1220 may add a predetermined massage pattern (for example, a massage pattern that may decrease the blood pressure or a massage pattern that may decrease the respiratory rate) to a portion of the preferred massage pattern of the user and/or may replace the portion of the preferred massage pattern of the user with the predetermined massage pattern (for example, a massage pattern that may decrease the blood pressure or a massage pattern that may decrease the respiratory rate) to determine a blood pressure control massage pattern.

Also, in a case in which blood pressure information of the user indicates a relatively high blood pressure, the blood pressure control massage pattern determining part 1220 may process the preferred massage pattern of the user to become gentler (and/or gradually gentler) to determine a blood pressure control massage pattern.

According to another embodiment of the present disclosure, the blood pressure control massage pattern determining part 1220 may acquire body composition information of the user, analyze the body composition information of the user to determine at least one of muscle mass and fat mass of the user, and additionally utilize at least one of the determined muscle mass and fat mass to determine a blood pressure control massage pattern.

The blood pressure control massage pattern determining part 1220 may acquire body composition information of the user. For example, the blood pressure control massage pattern determining part 1220 may acquire body composition information of the user from an external device or acquire body composition information of the user that is stored in the storage part 1500. Also, the blood pressure control massage pattern determining part 1220 may acquire body composition information of the user that is measured by the sensor part 1300 disposed in the massage apparatus 1000, but the present disclosure is not limited thereto. The body composition information acquired by the blood pressure control massage pattern determining part 1220 may include at least one of muscle mass and fat mass.

The blood pressure control massage pattern determining part 1220 may determine a blood pressure control massage pattern on the basis of at least one of muscle mass and fat mass.

For example, on the basis of at least one of the muscle mass and fat mass of the user, the blood pressure control massage pattern determining part 1220 may control mechanical stimuli that the massage module 1700 applies.

Specifically, in a case in which at least one of the muscle mass and fat mass of the user is low, the blood pressure control massage pattern determining part 1220 may select and/or process a massage pattern to determine a massage pattern, in which a distance between the massage module 1700 and the user is larger, as a blood pressure control massage pattern. In other words, in the case in which at least one of the muscle mass and fat mass of the user is low, the blood pressure control massage pattern determining part 1220 may adjust a massage pattern so that sympathetic nerves of the user are not activated and the intensity of the mechanical stimuli applied by the massage module 1700 is low.

Also, in a case in which at least one of the muscle mass and fat mass of the user is high, the blood pressure control massage pattern determining part 1220 may select and/or process a massage pattern to determine a massage pattern, in which the distance between the massage module 1700 and the user is smaller, as a blood pressure control massage pattern.

Different methods have been described separately for convenience of description, but the blood pressure control massage pattern determining part 1220 according to an embodiment of the present disclosure may utilize one or more of the above-described methods in combination to determine a blood pressure control massage pattern.

The audio determining part 1240 may determine a sound source to be provided together with a massage, on the basis of at least one of blood pressure information and heart rate information.

For example, in a case in which blood pressure information of a user indicates high blood pressure (and/or a case in which heart rate information of the user indicates a high heart rate), the audio determining part 1240 may select and/or process a sound source to determine a relatively slow sound source as a sound source to be provided together with a massage. Specifically, the audio determining part 1240 may determine a slow sound source among sound sources stored in the storage part 1500 as a sound source to be provided together with a massage or may decrease a tempo of a sound source stored in the storage part 1500 to determine the sound source as a sound source to be provided together with a massage, but the present disclosure is not limited thereto.

Also, on the basis of acquired blood pressure information (and/or heart rate information), the audio determining part 1240 may determine a voice instruction to be provided together with a massage. For example, in a case in which blood pressure information indicates high blood pressure (and/or a case in which heart rate information indicates high heart rate), the audio determining part 1240 may determine a respiratory guide voice instruction as a voice instruction to be provided together with a sound source. In this case, the audio determining part 1240 may utilize a respiratory guide voice instruction that is pre-stored in the storage part 1500 or may receive a respiratory guide voice instruction from an external device, but the present disclosure is not limited thereto.

The respiratory guide voice instruction refers to a voice that guides respiration. For example, the respiratory guide voice instruction may include voice instructions such as "Inhale slowly" and "Exhale slowly," but the present disclosure is not limited thereto.

The respiration of the user may become stable and the heart rate of the user may decrease due to the provided sound source and/or respiratory guide voice instruction, and as a result, the blood pressure of the user may be controlled.

According to an embodiment of the present disclosure, the blood pressure control massage pattern determined by the blood pressure control massage pattern determining part 1220 may include a warming function control pattern. In this case, the warming function control pattern may be determined on the basis of blood pressure information.

For example, in a case in which blood pressure information of a user indicates high blood pressure, the blood pressure control massage pattern may include a pattern in which the warming function is turned on for a predetermined amount of time. In a case in which the massage apparatus 1000 provides warmth, there may be an effect of stabilizing the sympathetic nerves and decreasing the blood pressure of the user.

According to an embodiment of the present disclosure, the massage providing part 1230 may control the massage module 1700 on the basis of the determined blood pressure control massage pattern. Also, on the basis of the determined blood pressure control massage pattern, the massage providing part 1230 may simultaneously control a calf massage module 1700 and/or a foot massage module 1700 disposed in the leg massage part. Also, on the basis of the determined blood pressure control massage pattern, the massage providing part 1230 may control at least one air cell and/or the warming function provided in the massage apparatus 1000. In addition, the controller 1200 may provide a sound source and/or a voice instruction determined by the audio determining part 1240 through the audio output module 1600 together with a massage.

Figure 4:
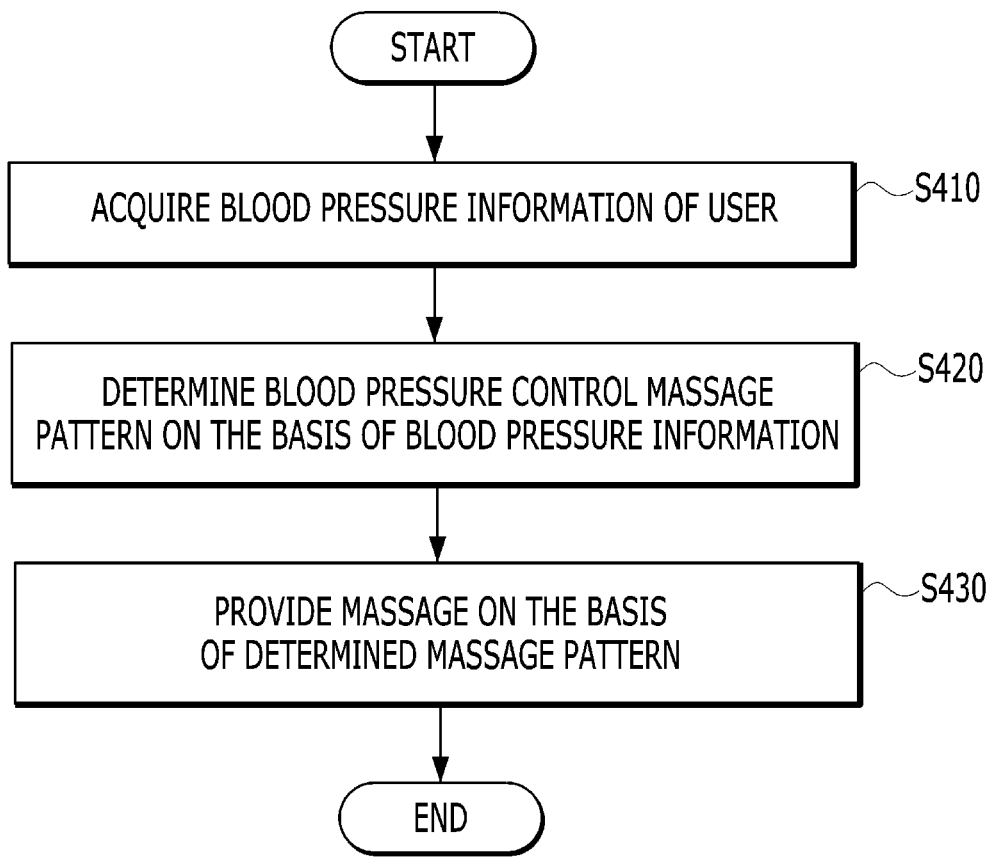
FIG. 4 is a view for describing a method for providing a blood pressure control massage according to an embodiment of the present disclosure.

FIG. 4 is a view for describing a method for providing blood pressure control massage according to an embodiment of the present disclosure.

In operation S410, the massage apparatus 1000 may acquire blood pressure information of a user. The method by which the massage apparatus 1000 acquires the blood pressure information of the user has been described above in detail with reference to FIG. 3.

In operation S420, the massage apparatus 1000 may determine a blood pressure control massage pattern on the basis of the blood pressure information. The method by which the massage apparatus 1000 determines the blood pressure control massage pattern has been described above in detail with reference to FIG. 3.

In operation S430, the massage apparatus 1000 may provide a massage to the user on the basis of the determined blood pressure control massage pattern. This has been described above in detail with reference to FIG. 3.

Figure 5:
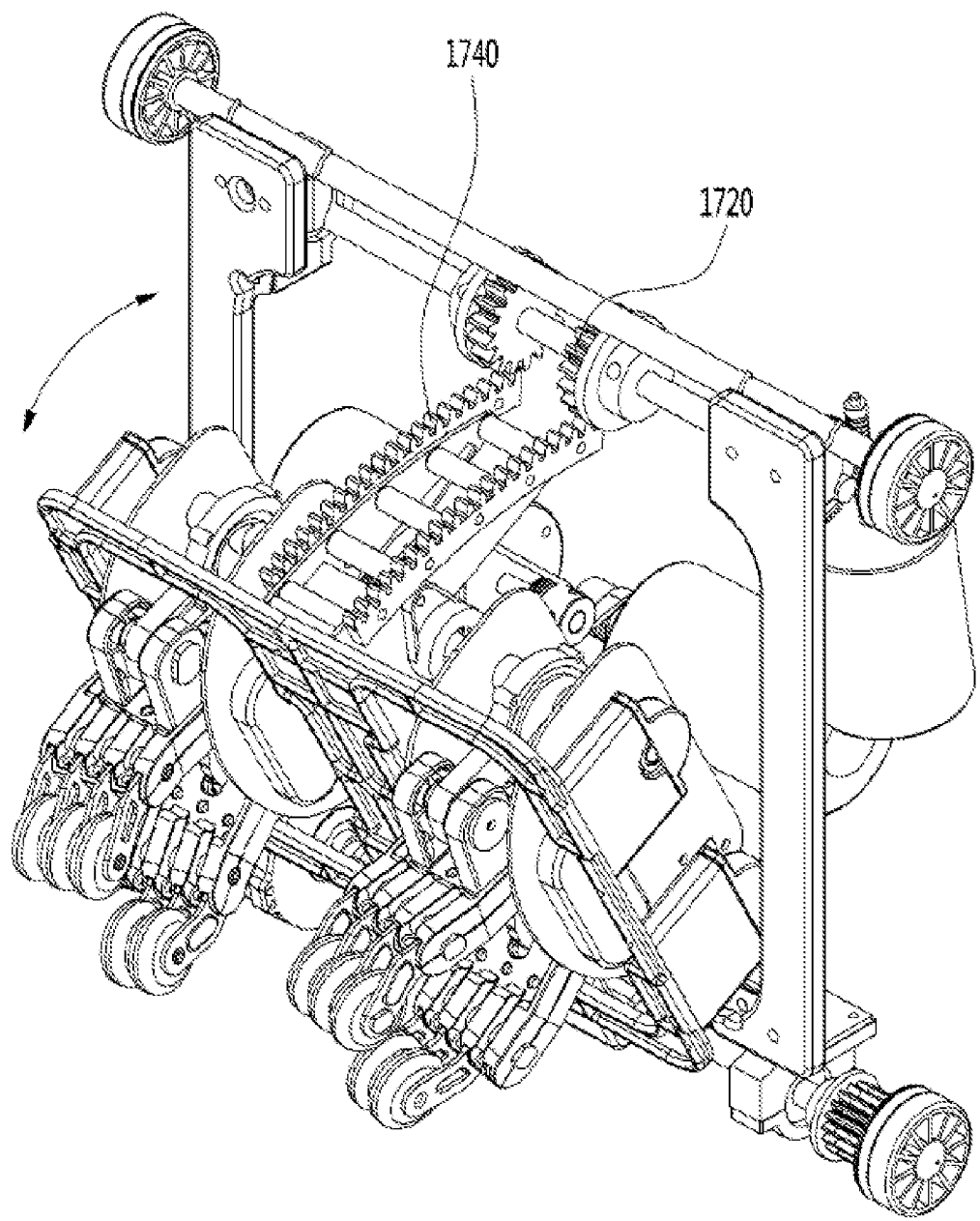
FIG. 5 is a view for describing a massage module according to an embodiment of the present disclosure.

FIG. 5 is a view for describing the massage module according to an embodiment of the present disclosure.

According to an embodiment of the present disclosure, the massage module 1700 may move forward or rearward to provide a massage.

For example, in the massage module 1700, a rack gear 1740 and a pinion gear 1720 engaged with the rack gear 1740 may be disposed in a front-rear direction. Also, in a case in which an actuator disposed in the massage module 1700 is operated due to control of the controller 1200, since the pinion gear 1740 moves along the rack gear 1720, the forward/rearward movement of the massage apparatus 1000 may be allowed.

According to an embodiment of the present disclosure, in a case in which at least one of muscle mass and fat mass of a user is low, a massage pattern in which the massage module 1700 is moved rearward may be provided to prevent the sympathetic nerves of the user from being activated.

According to another embodiment of the present disclosure, the size of the chest cavity increases and the chest is expanded forward upon inhalation, and the size of the chest cavity decreases and the chest is contracted rearward upon exhalation, and the massage apparatus 1000 may use the massage module 1700, which is able to move forward and rearward, to guide the respiration of the user and change the respiration of the user.

Those of ordinary skill in the art should well understand that the present disclosure may be implemented by combination of different program modules and/or combination of hardware and software. For example, the present disclosure may be implemented by a computer-readable medium.

Any computer-accessible medium may be the computer-readable medium, and the computer-readable medium includes volatile and nonvolatile media, transitory and non-transitory media, and removable and non-removable media. As a non-limiting example, the computer-readable medium may include a computer-readable storage medium and a computer-readable transmission medium.

The computer-readable storage medium includes volatile and nonvolatile media, transitory and non-transitory media, and removable and non-removable media that may be implemented using computer-readable instructions, a data structure, a program module, or any other arbitrary method or technology for storing information such as data. The computer-readable storage medium may include a RAM, a read-only memory (ROM), an electrically erasable and programmable read-only memory (EEPROM), a flash memory, or other memory technologies, a compact disk-read only memory (CD-ROM), a digital video disk (DVD), or other optical disk storage devices, a magnetic cassette, a magnetic tape, a magnetic disk storage device, or other magnetic storage devices, or any other arbitrary medium that is computer-accessible and may be used to store desired information, but the present disclosure is not limited thereto.

The computer-readable transmission medium generally implements a computer-readable instruction, a data structure, a program module, or any other data in a modulated data signal, such as a carrier wave and any other transport mechanism, and includes any information transmission medium. The term "modulated data signal" refers to a signal in which one or more characteristics of the signal is set or changed to encode information into the signal. As a non-limiting example, the computer-readable transmission medium includes wired media such as a wired network and or direct-wired connection and wireless media such as sound, RF, infrared light, and any other wireless medium.

Any arbitrary combination of the above-mentioned media also belongs to the range of the computer-readable transmission medium.

Those of ordinary skill in the art should understand that various exemplary logical blocks, modules, processors, means, circuits, and algorithm operations, which have been described in relation to the embodiments disclosed herein, may be implemented by electronic hardware, various forms of programs or design codes (which are referred to as "software" herein for convenience), or any combination thereof. In order to clearly describe the intercompatibility of hardware and software, in relation to functions thereof, various exemplary components, blocks, modules, circuits, and operations have been generally described above. Whether the functions are implemented as hardware or software depends on design constraints imposed on specific applications and the entire system. Those of ordinary skill in the art may implement the described functions using various methods for each specific application, but such implementation decisions should not be interpreted as deviating from the scope of the present disclosure.

Various embodiments proposed herein may be implemented as a manufactured article using a method, an apparatus, or standard programming and/or engineering technology. The term "manufactured article" includes a computer program accessible from an arbitrary computer-readable device, a carrier, or media. For example, the computer-readable storage medium may include a magnetic storage device (e.g., a hard disk, a floppy disk, a magnetic strip, etc.), an optical disk (e.g., a CD, a DVD, etc.), a smart card, and a flash memory device (e.g., an EEPROM, a card, a stick, a key drive, etc.), but is not limited thereto. The term "machine-readable medium" includes wireless channels and various other media capable of storing, retaining, and/or transmitting a command(s) and/or data, but is not limited thereto.

It should be understood that a specific order or hierarchical structure of operations in the proposed processes is an example of exemplary approaches. It should be understood that a specific order or hierarchical structure of operations in the processes may be rearranged within the scope of the present disclosure on the basis of design priorities. The attached method claims provide elements of various operations in a sample order, but this does not mean that the present disclosure is limited to the proposed specific order or hierarchical structure.

Description of the proposed embodiments has been provided above to allow anyone of ordinary skill in the art to use or embody the present disclosure. It should be apparent to those of ordinary skill in the art that various modifications may be made to the embodiments, and general principles defined herein may be applied to other embodiments without departing from the scope of the present disclosure. Therefore, the present disclosure is not limited to the embodiments proposed herein and should be interpreted as having the broadest possible range that is consistent with the principles and novel features proposed herein.

The invention claimed is:

1. A method for providing blood pressure control massage, the method comprising:
   receiving blood pressure information of a first user;
   receiving body composition information including at least one of muscle mass and fat mass of the first user;
   determining a blood pressure control massage pattern on the basis of the blood pressure information and the at least one of the muscle mass and the fat mass, wherein the determining the blood pressure control massage pattern on the basis of the blood pressure information and the at least one of the muscle mass and the fat mass includes:
  in a case in which the at least one of the muscle mass and the fat mass of the first user is lower than a second user, determining a massage pattern in which a massage module is farther away from the first user than the second user and intensity of a mechanical stimulus applied by the massage module is lower than that of the second user, and
  in a case in which the at least one of the muscle mass and the fat mass of the first user is higher than the second user, determining a massage pattern in which a massage module is closer toward the first user and the intensity of the mechanical stimulus applied by the massage module is higher than that of the second user; and
providing a massage on the basis of the blood pressure control massage pattern.

2. The method of claim 1, further comprising acquiring preferred massage pattern information of the first user, wherein the determining of the blood pressure control massage pattern includes utilizing the preferred massage pattern information of the first user to determine the blood pressure control massage pattern.

3. The method of claim 2, wherein, in a case in which the blood pressure information of the first user is higher than the second user, a preferred massage pattern of the first user becomes gradually slower.

4. The method of claim 2, wherein, in a case in which the blood pressure information of the first user is higher than the second user, at least a portion of a preferred massage pattern is replaced with a predetermined massage pattern that decreases a blood pressure.

5. The method of claim 1, wherein the receiving body composition information further comprises,
  receiving another body composition information of the user; and
  analyzing the another body composition information of the user to measure the at least one of muscle mass and fat mass of the user.

6. The method of claim 1, wherein,
in a case in which the blood pressure information of the first user is higher than or equal to a predetermined threshold value, determining a massage pattern, of which a speed is slower by a predetermined value, as the blood pressure control massage pattern.

7. The method of claim 1, wherein the blood pressure control massage pattern includes a respiratory guide pattern.

8. The method of claim 7, wherein the respiratory guide pattern is determined on the basis of respiratory rate information of the first user.

9. The method of claim 5, wherein the respiratory guide pattern is a massage pattern in which the massage module moves in a direction toward the first user to push the first user and in the direction opposite to the first user to guide respiration of the first user.

10. The method of claim 9, wherein, in a case in which the blood pressure information of the first user is higher than the second user, a number of times the massage module moves according to the respiratory guide pattern starts from a predetermined value and gradually decreases over time.

11. The method of claim 9, wherein, in a case in which the blood pressure information of the first user is higher than the second user, a number of times the massage module moves according to the respiratory guide pattern starts from a number of times that corresponds to an acquired respiratory rate and gradually decreases over time.

12. The method of claim 1, further comprising providing a sound source on the basis of at least one of the blood pressure information and heart rate information.

13. The method of claim 1, further comprising providing a respiratory guide voice instruction on the basis of at least one of the blood pressure information and heart rate information.

14. The method of claim 1, wherein the determining the blood pressure control massage pattern on the basis of the blood pressure information and the at least one of the muscle mass and the fat mass includes:
  classifying the blood pressure information into a plurality of groups; and
  determining the blood pressure control massage pattern on the basis of a group to which a blood pressure of the first user belongs.

15. A massage apparatus comprising:
  a controller configured to acquire blood pressure information of a first user, receive body composition information including at least one of muscle mass and fat mass of the first user, determine a blood pressure control massage pattern on the basis of the blood pressure information and the at least one of the muscle mass and the fat mass, and provide a massage on the basis of the blood pressure control massage pattern; and
  a massage module configured to provide a mechanical stimulus to at least a part of the first user's body according to control of the controller,
  wherein the controller:
    in a case in which the at least one of the muscle mass and the fat mass of the first user is lower than a second user, determines a massage pattern in which the massage module is farther away from the first user and intensity of the mechanical stimulus applied by the massage module is lower than that of the second user, and
    in a case in which the at least one of the muscle mass and the fat mass of the first user is higher than the second user, determines a massage pattern in which the massage module is closer toward the first user and the intensity of the mechanical stimulus applied by the massage module is higher than that of the second user.

16. The massage apparatus in claim 15, wherein the controller:
  receive another body composition information of the user; and
  analyze the another body composition information of the user to measure the at least one of muscle mass and fat mass of the user.

17. The massage apparatus in claim 15, wherein the controller:
  in a case in which the blood pressure information of the first user is higher than or equal to a predetermined threshold value, determines a massage pattern, of which a speed is slower by a predetermined value, as the blood pressure control massage pattern.

18. The massage module in claim 15, further comprising a rack gear;
  a pinion gear configured to engage with the rack gear, wherein a movement of the pinion gear in a direction toward the first user and in the direction opposite from the first user allows a movement of the massage apparatus in the direction toward the first user and in the direction opposite from the first user; and an actuator configured to operate according to the control of the controller.

19. The massage apparatus in claim 15, wherein the blood pressure control massage pattern includes a respiratory guide pattern in which the massage module moves in the direction toward the first user and in the direction opposite from the first user to push the first user and guide respiration of the first user.

20. The massage apparatus in claim 15, wherein the controller:
- in a case in which a blood pressure of the first user is higher than the second user, modifies at least a portion of the blood pressure control massage pattern to a massage pattern having a gradually decreasing intensity and speed.

* * * * *